United States Patent [19]
Ota et al.

[11] Patent Number: 5,160,979
[45] Date of Patent: Nov. 3, 1992

[54] TEST PIECE COLORATION COMPARATIVE DECISION UNIT

[75] Inventors: Hiroyuki Ota; Takao Terada, both of Osaka, Japan; Bernd G. Herpichboehm; George H. Sierra; Robert B. Summers; Thomas M. Watlington, all of Indianapolis, Ind.

[73] Assignees: Omrom Corp., Kyoto, Japan; Boehringer Mannheim Corp., Indianapolis, Ind.

[21] Appl. No.: 652,487

[22] Filed: Feb. 8, 1991

Related U.S. Application Data

[63] Continuation of Ser. No. 534,340, Jun. 6, 1990, abandoned, which is a continuation of Ser. No. 224,367, Jul. 26, 1988, abandoned.

[30] Foreign Application Priority Data

Jul. 27, 1987 [JP] Japan .................. 62-187322

[51] Int. Cl.⁵ .............................. G01J 3/52
[52] U.S. Cl. .................. 356/423; 364/413.11
[58] Field of Search ............. 356/42, 421–425; 434/98, 101; 364/413.09, 413.11, 526

[56] References Cited

U.S. PATENT DOCUMENTS 2,058,073 10/1936 Fritzsching .
4,685,059 8/1987 Yamamoto .................. 364/415
4,871,258 10/1989 Herpichboehm et al. .......... 356/422

FOREIGN PATENT DOCUMENTS

3428630A1 2/1985 Fed. Rep. of Germany .

*Primary Examiner*—F. L. Evans
*Attorney, Agent, or Firm*—Dickstein, Shapiro & Morin

[57] ABSTRACT

An apparatus is provided for making color comparisons between a test sample and a plurality of color samples. The color samples are arranged on a circle on a rotatable member and are successively moved into position adjacent a test sample. When an operator determines that a color sample adjacent the test sample is closest in color to the test sample he operates a switch which causes a stored numerical value associated with that sample to be read out and displayed on a display device.

8 Claims, 3 Drawing Sheets

TEST PIECE COLORATION COMPARATIVE DECISION UNIT

This application is a continuation of application Ser. No. 07/534,340, filed Jun. 6, 1990, now abandoned which is a continuation of Ser. No. 07/224,367 filed Jul. 26, 1988, now abandoned.

BACKGROUND OF THE INVENTION

1. Field of the Invention

This invention relates to a unit for deciding the coloration of a test piece by comparison with reference samples. Such a unit is typically used for biochemical tests (such as a urine sugar test, a blood sugar test, or a urobilin test) and is hereinafter referred to as "a test piece coloration comparative decision unit", when applicable. More particularly, the invention relates to a test piece coloration comparative decision unit which is used for making a decision concerning the coloration of a test sheet (reagent part) impregnated, for instance, with urine which test sheet is then compared with a plurality of reference sample colors in order to determine sugar content in the urine.

2. Discussion of the Prior Art

Heretofore, in a biochemical test for urine or the like, the coloration of a test sheet is determined by a non-electronic color comparative decision system in which an operator visually reads the coloration of the test sheet, or with an electronic urine sugar meter (an electronic biochemical measuring instrument) which comprises, for example a reflection sensor, for automatically reading and displaying the result of a test sheet coloration.

FIG. 4 is a perspective view showing a conventional non-electronic test piece coloration comparative decision unit. It comprises: a cylindrical case 72 with a cap 71; and a sheet-shaped comparing color sample part 73 bonded to the cylindrical outer wall of the case 72. A number of test sticks (each comprising a resin sheet, and a test sheet 75 impregnated with a reagent and bonded to one end of the resin sheet) 74 are accommodated in the cylindrical case 72. In a urine sugar test, the cap 71 is removed from the cylindrical case 72, and a test stick 74 is taken out of the case 72. Then, the test sheet 75 is impregnated with urine. Upon impregnation with urine, the test sheet 75 shows a color reaction according to the content of sugar in the urine. The color of the test sheet 75 thus treated is compared with various colors provided in the comparing color sample part 73 on the cylindrical case 72, for the purpose of deciding the coloration of the test sheet. That is, in the color sample part 73, various color samples (for negative and positive signs) 73a provided separately according to the content of sugar (grape sugar) in urine are arranged in a plurality of lines. The color of the test sheet 75 thus treated is compared with the variety of colors 73a in the color sample part 73 in order to find the same color (or a color substantially similar thereto), whereby the coloration is determined. More specifically, it is determined whether the content of sugar in the urine is more or less than a standard (or negative or positive).

In an electronic biochemical measuring device, such as a urine sugar meter, a reflection sensor is used which includes a light emitting element and a light receiving element. In this device, light is applied to the coloration test sheet by the light emitting element (such as a light emitting diode), and light reflected from the test sheet is received by the light receiving element (such as a photo-transistor), so that the urine sugar value is automatically displayed in a digital mode according to the received color reaction light quantity.

The first described, non-electronic, test piece coloration comparative decision unit is formed merely by bonding the sheet-shaped color sample part to the outer cylindrical wall of the test stick accommodating case (i.e., the cylindrical case). Therefore, for a color comparison, the test stick impregnated with the urine is held with the fingers and placed successively beside the various colors in the color sample part until the same color as the test sheet or a color similar that of the test sheet is found. That is, in the color comparison, the operator must incrementally move in fine steps the test sheet impregnated with the urine, i.e., the used test sheet, along the color sample part with a very small gap between the color sample part and the test sheet which requires considerable dexterity. Furthermore, in the color comparison, the test sheet is liable to shift from the color sample, and therefore it can be difficult for an operator to accurately decide the delicate color difference between various colors of the color sample part.

In the electronic biochemical measuring unit (such as a urine sugar meter) the reflection sensor receives the color reaction light quantity of the test sheet, and the sugar value is automatically displayed according to the color reaction light quantity thus received. Therefore, with this device, the labor and time required for operation of the coloration comparative decision unit, and the operation of referring a mean value (urine sugar value) of a selected color to a comparison table to decide a color value (or a negative sign or positive sign) can be eliminated. However, the electronic biochemical measuring unit is disadvantageous in that, since it employs a reflection sensor, it is expensive, and is also sometimes difficult to accurately detect the delicate coloration of the test sheet with this device.

SUMMARY OF THE INVENTION

Accordingly, an object of this invention is to provide a test piece coloration comparative decision unit in which the coloration of a test sheet is visually compared with a plurality of color samples, and the mean value of a color sample which is the same as or similar to the color of the test sheet and which is selected through the visual color comparison is displayed on a display device, thus providing a test piece coloration comparative decision unit which is accurate, relative inexpensive, and which can automatically display the result of the coloration comparison.

The foregoing object of the invention has been achieved by the provision of a test piece coloration comparative decision unit which comprises: a stationary insertion member into which the coloration test sheet of a test stick is inserted, a rotatable comparing color sample member, which preferably has a plurality of windows which are rotatable to a position adjacent to the stationary insertion member such that as the color sample member rotates the coloration test sheet appears successively in each window, a plurality of different color samples provided adjacent to the windows, respectively, the windows and different color samples being arranged in the form of coaxial circles; means for selecting a color sample which is adjacent a test sheet and associated with the window through which the test sheet is viewable; memory means for storing the mean values of the different color samples in advance; and display means for displaying the mean value of the color sample thus selected.

The memory means for storing the mean values (such as urine sugar values) of the different color samples is provided in the comparative decision unit body. In use, an operator visually compares the color of the test sheet appearing in each of the windows with the different color samples arranged adjacent to the windows, and thus the test sheet, while rotating the comparing color sample member. When it is determined that the test sheet is equal or almost equal in color to a color sample, that color sample is selected. That is, at this time instant, the operator depresses a comparison result determining switch. While the comparing color sample member is being rotated by the operator, a position detecting means (such as a micro-switch) detects the position of each of the color samples with respect to a reference position, so that the color sample selected as equal or substantially equal in color to the test sheet can be determined at the time the comparison result determining switch is depressed.

In response to the depression of the comparison result determining switch, the mean value (for instance urine sugar value) of the color sample thus determined is automatically read out of the memory means and displayed on the display device. That is, since the operator visually compares the color of the test sheet with the different color samples, a delicate color comparison can be achieved with high accuracy. Furthermore, since the mean value (urine sugar value) of the color sample is automatically read out and displayed, the time and labor required for reading the mean value of a color sample from e.g., a table of results, can be eliminated.

BRIEF DESCRIPTION OF THE DRAWINGS

The above and other objects, advantages and features of the invention will become more readily apparent from the following detailed description of the invention which is provided in connection with the accompanying drawings, in which.

DETAILED DESCRIPTION OF THE INVENTION

Figure 2:
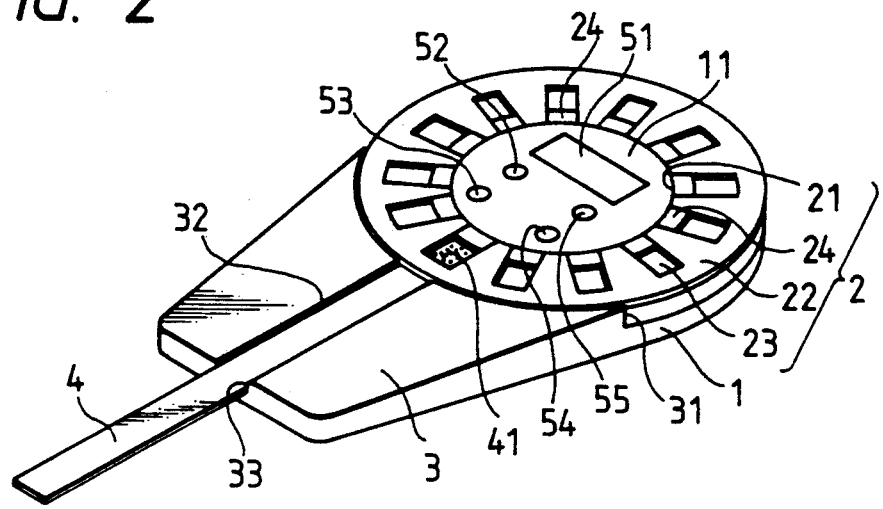
FIG. 2 is a perspective view of the test piece coloration comparative decision unit according to the invention.

FIG. 2 is a perspective view showing one example of a test piece coloration comparative decision unit according to this invention.

The coloration comparative decision unit comprises a stationary disc 1 having a colored test piece mounting stand 3; and a comparing color sample member 2 rotatably mounted on the stationary disc 1.

The stationary disc 1 is in the form of a flat disc which has a hollow mounting part 11 protruding from the central portion of the disc, and the colored test piece mounting stand 3 is in the form of a rectangular flat plate extending radially outwardly from a part of the periphery of the disc 1. The junction of the stand 3 and the disc 1 has an arcuate step 31 arranged along substantially a half of the circumference of the disc 1. The arcuate step 31 is formed because the colored test piece mounting stand is larger in thickness than the stationary disc 1. This arcuate step 31 contributes to the rotation of the comparing color sample part 2 (as described later). A groove 32 substantially U-shaped in section is formed in the upper surface of the colored test piece mounting stand 3 in such a manner that it is extended towards the hollow mounting part 11. The bottom of the groove 32 thus formed is employed as a test stick mounting part (or a test piece mounting stand) 33. A test stick 4 (formed, for example, by bonding a reagent-impregnated test sheet 41 to one end portion of a resin sheet) is placed on the test stick mounting part 33. The base end of the test stick mounting part 33 merges with the colored test piece mounting stand 3, while the top end thereof is adjacent to the stationary disc 1, but it is not connected to the stationary disc 1, whereby it can be elastically bent with the base end as the fulcrum; that is, it has an elastic restoring force.

The above-described hollow mounting part 11 is in the form of a cylinder having a small height. An electronic circuit (described later) is built inside the hollow mounting part 11 and a display device 51, a power switch 52, a decision switch 53, a memory switch 54, and a start switch 55 are provided on the top surface of the hollow mounting part 11.

The comparing color sample member 2 is a ring-shaped flat disc 22 having an engaging hole at the center. The ring-shaped flat disc 22 is rotatably fitted o the hollow mounting part 11 of the stationary disc 1. A plurality of windows 23 are formed in the outer peripheral portion of the flat disc 22 at equal angular intervals, and different color samples 24 are provided on the flat disc 22 at equal angular intervals in correspondence to the windows 23, respectively, in such a manner that the windows 23 are so positioned that, when the comparing color sample member 2 is mounted on the hollow mounting part 11, the test sheet 41 of the test stick 4 appears in a window 23. Thus, each of the color samples is rotatable into a position where it is adjacent the test sheet for a color comparison. The different color samples 24 have different colorations which are provided separately according to the different possible contents of sugar in urine; that is, colors meaning negative and positive signs are arranged in the form of a circle.

Figure 3:
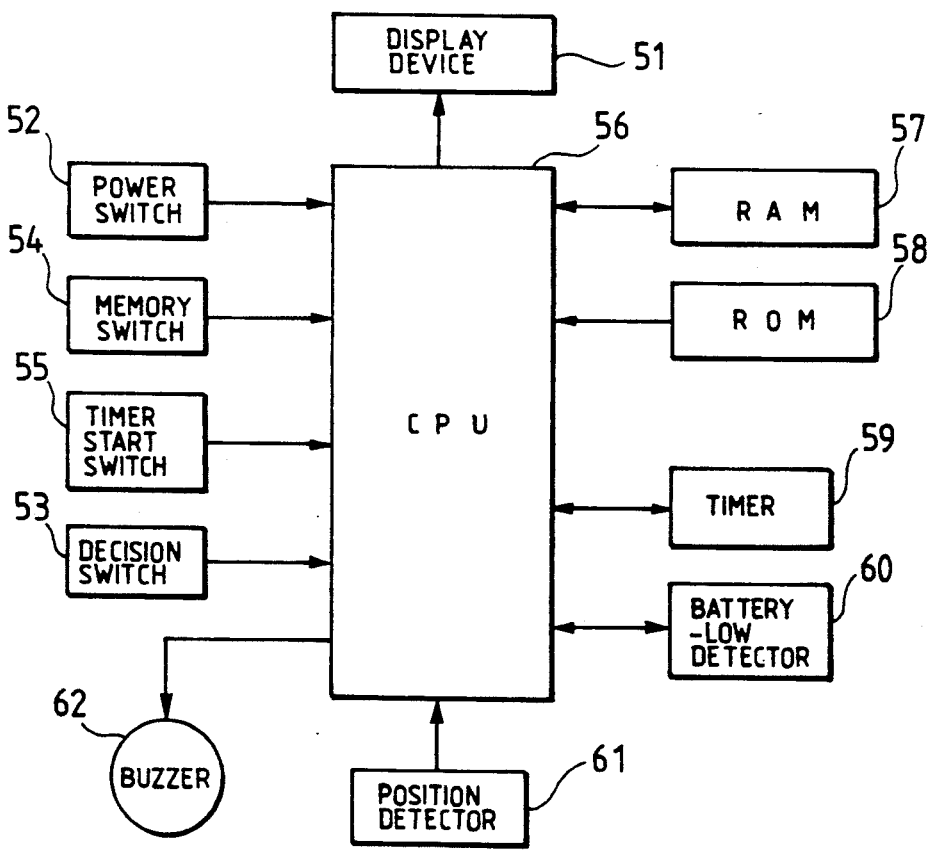
FIG. 3 is a block diagram showing an electronic circuit provided for the test piece coloration comparative decision unit of the invention.
Figure 4:
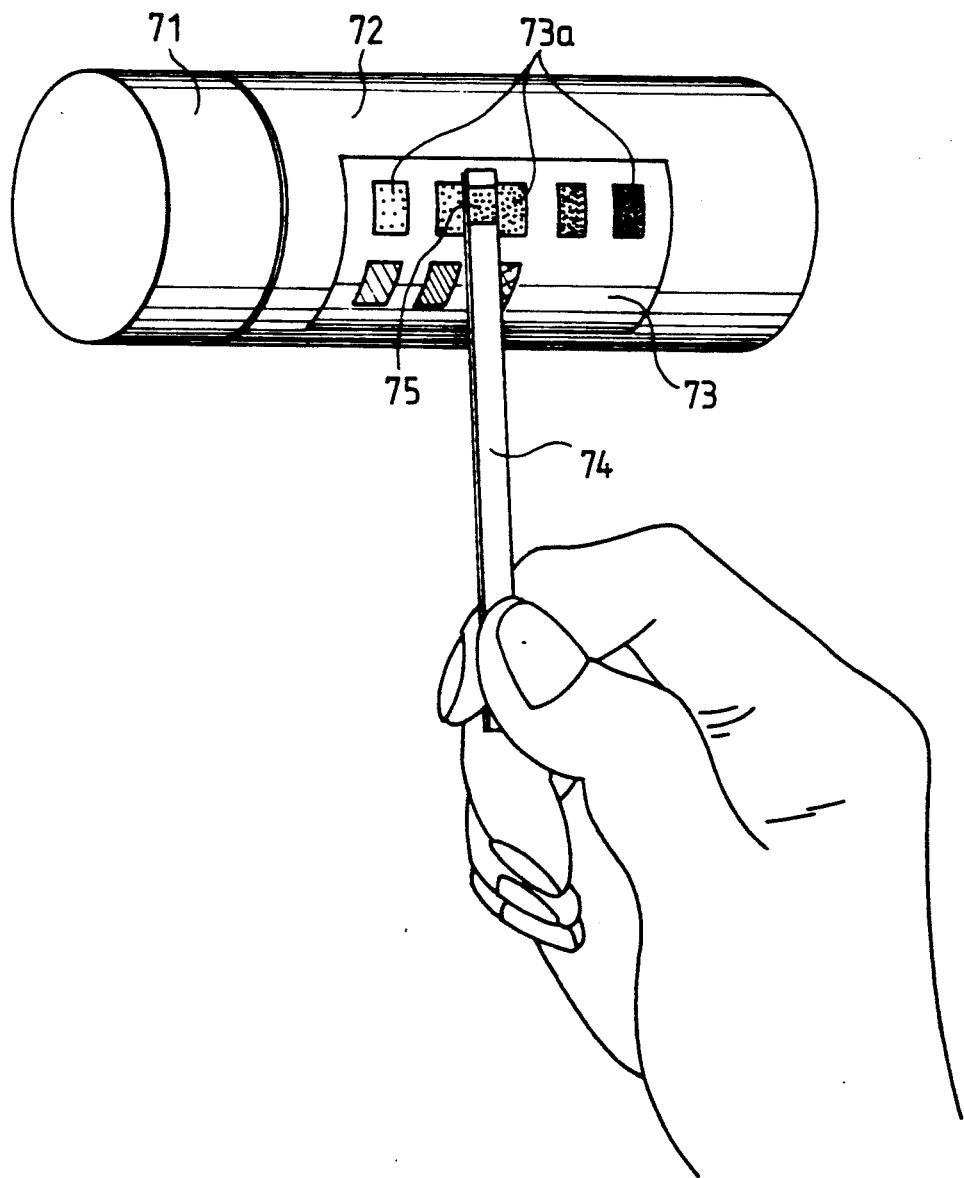
FIG. 4 is a perspective view showing a conventional coloration comparative decision unit.

FIG. 3 is a block diagram showing one example of the circuit which forms the test piece coloration comparative decision unit of the invention.

As was described above, the display device 51, the power switch 52, the decision switch 53, the memory switch 54, and the start switch 55 are provided on the top surface of the above-described hollow mounting part 11. A CPU (central processing unit) 56, a RAM (random access memory) 57, and ROM (read-only memory) 58, a timer 59, and a battery-low detector 50 are built inside the hollow mounting part 11.

A control program executed by the CPU 56, described below and the mean values of the different color samples 24 are stored in the ROM 58. The mean values of the different color samples 24 are the numbers of the color samples 24 and the values (for instance urine sugar values) corresponding to the numbers which are stored in the form of a table. The RAM 57 is a non-volatile memory for storing the results of measurement (urine sugar values). The timer 59 starts counting the time required for performing the coloration comparative decision in response to the operation of the start switch 55, and operates a buzzer 62 providing an audible sound when a predetermined period of time has expired. The battery-low detector 60 detects whether or not the battery is serviceable, and, when the voltage of the battery is lower than a predetermined value, causes the display device 51 to display an indication of the same.

The decision switch 53 is operated by the operator as follows: The operator visually compares the coloration of the test sheet 41 with the color samples 24, as each is moved into a position adjacent the test sheet 41 during rotation of color sample member 2, and when he determines that the test sheet 41 is equal, or substantially equal, to one of the color samples, the decision switch is operated to specify that the color sample 24 then adjacent the test sheet 41 is the closest in color to that of test sheet 41. A position detector 61, for instance a micro-switch, detects, during the rotation of the comparing color sample member 2, the angular positions of the different color samples 24. Protrusions (not shown) are formed on the lower surface of the flat disc 22 in correspondence to the color samples 24, respectively, so that the micro-switch counts the protrusions passing through a reference position as the flat disc 22 bearing the color samples 24 is turned, thereby to detect the angular positions of the color samples 24. As a result, when the flat disc 22 is stopped, the color sample 24 then aligned with and adjacent to the test sheet 41 can be determined. Instead of the micro-switch system described above, different codes can be assigned to the different color samples 24, so that the color sample codes are optically read while the flat disc 22 is being turned, whereby, when the flat disc 22 is stopped and switch 53 is depressed, the color sample 24 aligned with the test sheet 41 is determined.

The memory switch 54 is operated by the operator in order to read out previously determined and stored values (urine sugar values) which are read out of the RAM 57 and displayed on the display device 51.

When the position decision switch 54 is depressed and a color sample 24 is selected and determined by the position detector 61, the CPU 56 reads the value (urine sugar value) corresponding to the color sample 24 thus determined out of the ROM 58, and displays it on the display device 51, and stores it in the RAM 57.

Figure 1:
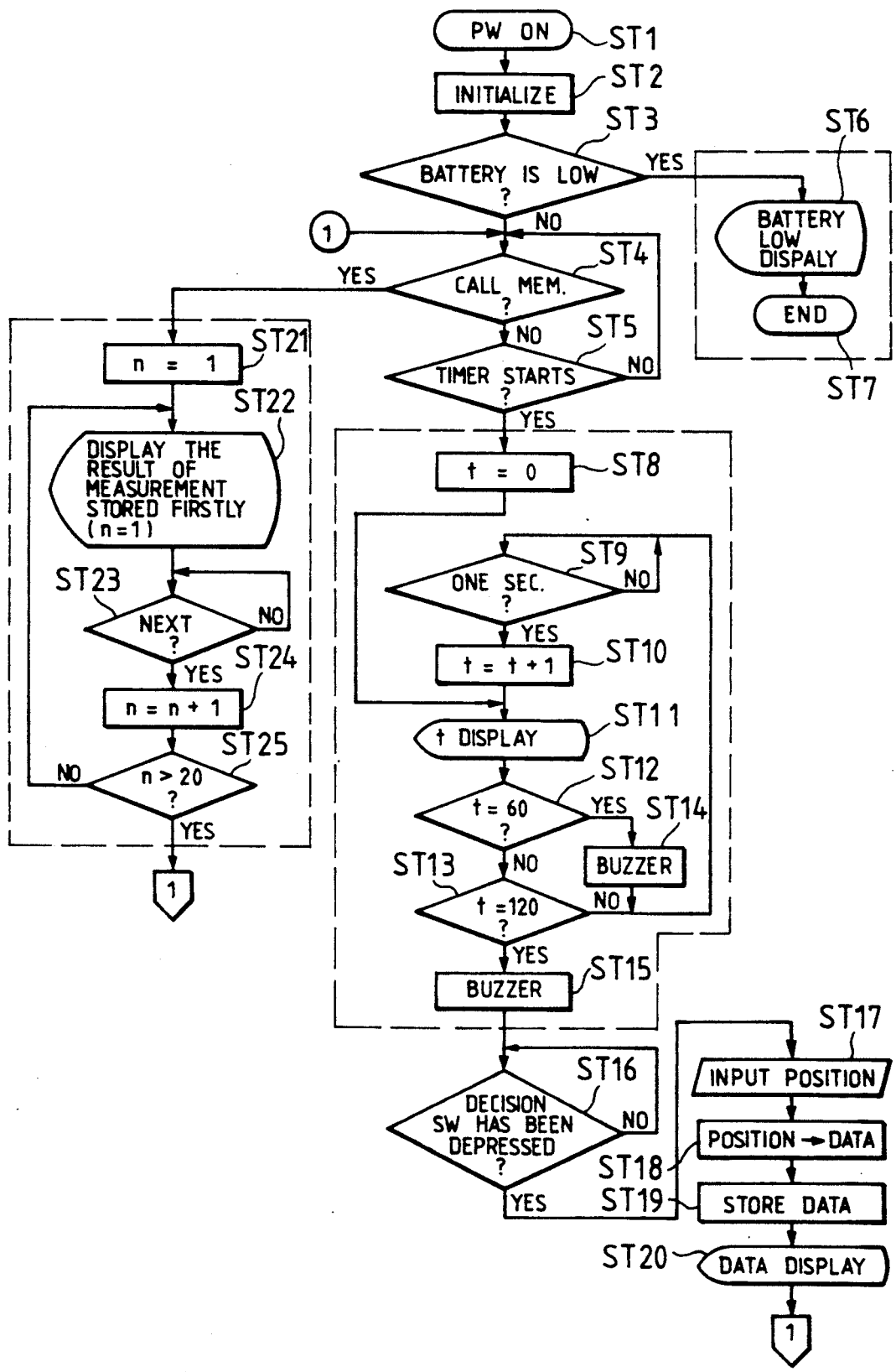
FIG. 1 is a flow chart illustrating the operation of an exemplary test piece coloration comparative decision unit according to this invention.

FIG. 1 is a flow chart showing the operation of the test piece coloration comparative decision unit.

When the operator turns on the power switch 52 ( in step 1 (hereafter referred to as "ST", when applicable) the comparative decision unit is initialized (ST 2), and it is determined whether or not the battery is serviceable (ST 3). If the voltage of the battery is lower than a predetermined value, then in step ST 3 the result of decision is "Yes", and the low voltage of the battery is displayed on the display device 51 (ST 6). In this case, the measurement cannot be carried out (ST 7). When the battery is serviceable, then in step ST 3 the result of decision is "no", the following step ST 4 is executed, in which is it determined whether or not the memory switch 54 is depressed. That is, it is determined whether or not the operator has depressed the memory switch 54 to call and display the result of a previous measurement.

When a new measurement is to be performed, i.e., the memory switch 54 is not depressed, but the start switch 55 is depressed, the result of the decision in step ST 4 is "No", and the result of decision in step ST 5 is "yes". Thus when the start switch 55 is turned on, the timer 59 is set to zero (ST 8), whereupon a time counting operation is started, and the time counted is displayed on the display device 51 (ST 11). That is, a work time (60 seconds) required for applying urine to the test sheet 41 and wiping the surplus of urine off the test sheet 41 is counted. During the work time, the time counted is incremented every second through ST 9 and ST 10, and is successively displayed (ST 11). When sixty (60) seconds has elapsed since the start of the timer, the result of decision in ST 12 becomes "Yes", so that a buzzer is actuated to emit an audible sound telling the operator to place the test stick on the test stick mounting stand 33 (ST 14). Under this condition, in step ST 13 it is detected whether or not 120 seconds has passed since the start of the timer; that is, the coloration comparative decision unit is placed in standby state for a period of time which is required for the color reaction of the test sheet 41. When 120 seconds has passed, in step ST 13 the result of decision becomes "Yes", and the buzzer again activated to emit an audible sound alerting the operator to compare the color of the test sheet 41 with the color samples 24 (ST 15). Under this condition, the operator evaluates the comparing color sample member 2 and visually compares the color of the test sheet 41 appearing successively in the windows 23 with the color samples provided adjacent to the windows 23 and thus successively adjacent to the test sheet; that is, he selects a color sample 24 which is most similar to the color of the test sheet 4, while rotating the comparing color sample member 2.

Upon selection of one color sample 24 in this manner, the operator stops the rotation of the comparing color sample member 2, and depresses the decision switch 53. While the operator rotates the comparing color sample member 2 to find the color sample 24 which is equal or similar in color to the test sheet 41, the position detector (micro-switch) 61 detects each of the different color samples 24 which are moved by the rotation of the comparing color sample part. In step ST 16, it is determined whether or not the decision switch 53 has been depressed. When the decision switch 53 has been depressed, the result of determination in step ST 16 is "Yes", and the color sample 24 detected by the position detector is determined (ST 17). The value (urine sugar value) corresponding to the color sample thus determined is read out of the table in the ROM 58 (ST 18), and is then stored in the RAM 57 (ST 19). At the same time, the value thus read and stored is displayed in a digital mode on the display device 51 (ST 20).

When, after the above-described measurement has been repeatedly carried out, it is desired to confirm the results of past measurements, the memory switch 54 is depressed. As a result, the result of the decision in step ST 4 is "Yes", and the results of the color comparison measurements performed before and stored in the RAM 57 are displayed, in the order of storage, on the display device 51. In other words, upon the first depression of the memory switch 54, the result of the measurement stored firstly (n=1) is selected (ST 21) and displayed on the display device 51 (ST 22); and upon the second depression the memory switch 54, the result of determination in step ST 23, in which it is determined whether or not the next memory is selected, becomes "Yes", so that the result of the measurement stored secondly (n=n+1) is selected (ST 24) and displayed on the display device 51; and so forth. In the above-described embodiment, the results (data values) of twenty prior measurements are stored and can be displayed. Therefore, after the result of the twentieth (20th) measurement has been displayed, the memory calling operation is ended (ST 25).

As described above, in the coloration comparative decision unit of the invention, the comparing color sample member having the windows in which the test sheet appears and the different color samples provided adjacent to the windows, respectively is rotatable, and the coloration of the test sheet viewed through the windows is visually compared with the different color samples so that a color sample equal or substantially similar to the coloration of the test sheet is selected, and the mean value of the color sample thus selected is read out of the memory and displayed on the display device. Therefore, a delicate color comparison can be achieved with high accuracy, and the mean value of the color sample thus selected can be automatically displayed on the display device.

Accordingly, with the coloration comparative decision unit of the invention, the color comparison is easier to perform and is more accurate than the operation of confirming the mean values of the color samples by using a numerical table. Furthermore, in the coloration comparative decision unit of the invention, unlike the electronic biochemical measuring device, instead of the reflection sensor, a visual comparison is employed for color comparison. Thus, the coloration comparative decision unit provided according to the invention allows an accurate determination of delicate color differences and is low in manufacturing cost and easily operated.

While the invention has been described and illustrated in connection with a preferred embodiment, it should be apparent that many modifications can be made without departing from the spirit or scope of the invention. Accordingly, the invention is not limited by the foregoing description, but is only limited by the scope of the appended claims.

We claim:

1. A color comparative decision apparatus comprising:
   a stationary mounting member having an area for mounting a coloration test sample;
   a rotatable color sample member mounted on said stationary member and having a plurality of different color samples which are arranged in the form of a circle on said color sample member, said color samples being successively movable to a position adjacent said mounting area, upon rotation of said color sample member;
   means responsive to rotation of said color sample member for identifying a color sample which is adjacent said mounting area;
   first memory means for storing values representing each of said different color samples; and
   display means for displaying a stored color sample value corresponding to a color sample which is identified by said identifying means as being adjacent said mounting area.

2. A color comparative decision apparatus as in claim 1 further comprising first operator manipulatable switch means, means responsive to operation of said first switch means for (i) determining which of said color samples is adjacent said mounting area, (ii) retrieving a value representing the color sample determined to be adjacent said mounting area from said memory, and (iii) causing said display means to display said retrieved value.

3. A color comparative decision apparatus as in claim 2 further comprising second memory means for storing a predetermined number of values representing color samples which were previously retrieved from said first memory means and displayed, and second operator actuated switch means for causing a display on said display means of one or more of the values stored in said second memory means.

4. A color comparative decision apparatus as in claim 1 further comprising means for initiating a color comparison measurement, timer means for counting the time from initiation of a color comparison measurement, and means for causing the time counted by said timer means to be displayed on said display means.

5. A color comparative decision apparatus as in claim 4 wherein the apparatus includes means for providing an audible signal when said timer means counts to a first predetermined value.

6. A color comparative decision apparatus as in claim 5 wherein said timer means continues counting time after said first predetermined value is reached until a second predetermined value is reached after which audible signal producing means produces another audible signal.

7. A color comparative decision apparatus as in claim 3 further comprising means responsive to operator manipulation of said second switch means to cause a sequential display of the values stored in said second memory on a first stored, first displayed basis.

8. A color comparative decision apparatus as in claim 1 further comprising a plurality of windows provided in said rotatable color sample member in respective association with said color samples, said windows being arranged in the form of another circle on said color sample member coaxial with the circle of samples, each of said windows overlying said mounting area when its associated color sample is adjacent thereto so that a test sample mounted on said mounting area is viewable through a window.

* * * * *